United States Patent [19]

Wannamaker et al.

[11] Patent Number: 5,084,461
[45] Date of Patent: Jan. 28, 1992

[54] AZADECALIN AMIDES AND THIOAMIDES AS INHIBITORS OF CHOLESTEROL BIOSYNTHESIS

[75] Inventors: Marion W. Wannamaker, West Chester; William A. Van Sickle, Cincinnati; William R. Moore, Fairfield, all of Ohio

[73] Assignee: Merrell Dow Pharmaceuticals Inc., Cincinnati, Ohio

[21] Appl. No.: 676,149

[22] Filed: Mar. 27, 1991

[51] Int. Cl.$^5$ .................... A61K 31/47; C07D 217/06
[52] U.S. Cl. ................................. 514/307; 546/146
[58] Field of Search .................... 546/146; 514/307

[56] References Cited

U.S. PATENT DOCUMENTS 4,565,819  1/1986  Vincent et al. .................. 546/146
4,857,648  8/1989  Broger et al. .................... 546/146

Primary Examiner—Jane T. Fan
Assistant Examiner—James H. Turnipseed
Attorney, Agent, or Firm—Louis J. Wille

[57] ABSTRACT

The present invention provides certain novel azadecalin amides and thioamides which are useful as inhibitors of cholesterol biosynthesis and as agents which lower total serum cholesterol in patients in need thereof.

9 Claims, No Drawings

AZADECALIN AMIDES AND THIOAMIDES AS INHIBITORS OF CHOLESTEROL BIOSYNTHESIS

BACKGROUND OF THE INVENTION

The present invention relates to certain novel Azadecalin amides and thioamides which are useful as inhibitors of cholesterol biosynthesis and as agents which lower total serum cholesterol in patients in need thereof. The present invention also provides pharmaceutical compositions for the use of these novel compounds.

The conversion of the acyclic polyolefin squalene to the cyclic steroid lanosterol is a key step in the biogenesis of cholesterol. This conversion occurs in two steps. Squalene epoxidase catalyzes the conversion of squalene to (3S)-2,3-oxidosqualene. Oxidosqualene cyclase then converts (3S)-2,3-oxidosqualene to lanosterol. Lanosterol is converted through a number of subsequent enzymatic steps to cholesterol. Inhibition of squalene epoxidase decreases the amount of oxidosqualene available for conversion to cholesterol. Inhibition of oxidosqualene cyclase decreases the amount of lanosterol available for conversion to cholesterol. Inhibition of squalene epoxidase and/or oxidosqualene cyclase thus results in a decrease in the amount of cholesterol synthesized and ultimately causes a lowering of cholesterol in the blood.

Atherosclerosis as manifested in its major clinical complication, ischaemic heart disease, continues to be a major cause of death in industrialized countries. It is now well accepted that atherosclerosis can begin with local injury to the arterial endothelium followed by proliferation of arterial smooth muscle cells from the medial layer to the intimal layer along with deposition of lipid and accumulation of foam cells in the lesion. As the atherosclerotic plaque develops it progressively occludes more and more of the affected blood vessel and can eventually lead to ischaemia or infarction. Therefore, it is desirable to provide methods of inhibiting the progression of atherosclerosis in patients in need thereof.

There is now a large body of evidence demonstrating that hypercholesterolemia is an important risk factor associated with heart disease. For example, in December 1984, a National Institute of Health Consensus Development Conference Panel concluded that lowering definitely elevated blood cholesterol levels (specifically blood levels of low-density lipoprotein cholesterol) will reduce the risk of heart attacks due to coronary heart disease. Accordingly, it is desirable to provide a method for reducing blood cholesterol in patients with hypercholesterolemia.

Typically, cholesterol is carried in the blood of warm-blooded animals in certain lipid-protein complexes such as chylomicrons, very low density lipoprotein (VLDL), low density lipoprotein (LDL), and high density lipoprotein (HDL). It is widely accepted that LDL functions in a way that directly results in deposition of the LDL cholesterol in the blood-vessel wall and that HDL functions in a way that results in the HDL picking up cholesterol from the vessel wall and transporting it to the liver where it is metabolized [Brown and Goldstein, Ann. Rev. Biochem. 52, 223 (1983); Miller, Ann. Rev. Med. 31, 97 (1980)]. For example, in various epidemiologic studies the LDL cholesterol levels correlate well with the risk of coronary heart disease whereas the HDL cholesterol levels are inversely associated with coronary heart disease [Patton et al., Clin. Chem. 29, 1890 (1983)]. It is generally accepted by those skilled in the art that reduction of abnormally high LDL cholesterol levels is effective therapy not only in the treatment of hypercholesterolemia but also in the treatment of atherosclerosis.

The novel azedcalin amides and thioamides of the present invention are inhibitors of squalene epoxidase and/or oxidosqualene cyclase. These compounds thus inhibit cholesterol biosynthesis and are useful in lowering blood cholesterol in patients in need thereof.

In addition, many fungi, including *Microsporum canis, Ctenomyces mentagrophytes, Trichophyton rubrum, Phialophora verrucosa, Cryptococcus neoformans, Candida tropicalis, Candida albicans,* Mucor species, *Aspergillus fumigatus, Sporotrichum schenckii* and Saprolegnia species, are dependent on the biosynthesis of endogenous ergosterol for their growth and reproduction as described in "Chemical Activities of Fungi" by J. W. Foster (Academic Press Inc. 1949). Inhibition of ergosterol biosynthesis provides an antifungal effect in that it prevents the growth and reproduction of these fungi. The novel azadecalin amides and thioamides of the present invention inhibit ergosterol biosynthesis and thus are useful as antifungal agents.

SUMMARY OF THE INVENTION

The present invention relates to novel compounds of the formula (I)

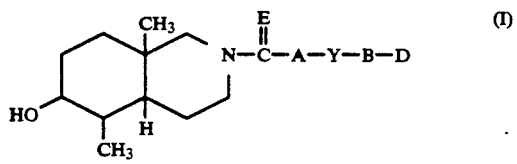

wherein
E is O or S;
A is a saturated $C_1$-$C_{14}$ alkylene of straight or branched chain configuration;
Y is oxygen, sulfur, sulfinyl or sulfonyl;
B is saturated $C_1$-$C_{14}$ alkylene of straight or branched chain configuration; and
D is a $C_1$-$C_4$ saturated or unsaturated alkyl of straight or branched chain configuration, —$CF_3$, —$CHF_2$, —$CH_2F$, or phenyl.

The present invention also relates to novel compounds of the formula (II)

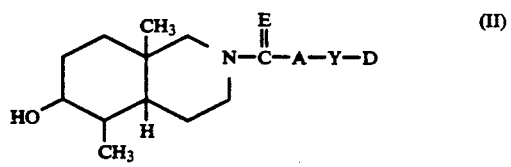

wherein
E is O or S;
A is a $C_1$-$C_{14}$ saturated alkylene of straight or branched chain configuration;
Y is a a oxygen, sulfur, sulfinyl or sulfonyl; and
D is a $C_1$-$C_4$ saturated or unsaturated alkyl of straight or branched chain configuration, —$CF_3$, —$CHF_2$, —$CH_2F$, or phenyl.

The present invention also relates to novel compounds of formula (III)

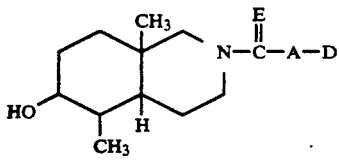

wherein
E is O or S;
A is a $C_1$-$C_{14}$ saturated alkylene of straight or branched chain configuration;
D is a $C_1$-$C_4$ saturated or unsaturated alkyl of straight or branched chain configuration, —$CF_3$, —$CHF_2$, —$CH_2F$, or phenyl.

The present invention also relates to novel compounds of formula (IV)

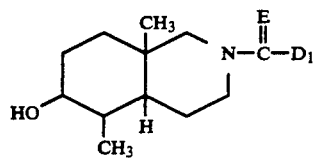

wherein
E is O or S;
$D_1$ is H, —$CF_3$, —$CHF_2$, $CH_2F$, —$CH_3$ or phenyl.

The present invention further provides a method of inhibiting the biosynthesis of cholesterol in a patient in need thereof comprising administering to said patient an effective cholesterol biosynthesis inhibitory amount of a compound of formula (I), compound of formula (II), compound of formula (III), or compound of formula (IV).

The present invention also provides a method of lowering plasma cholesterol in a patient in need thereof, and a method of treating a patient afflicted with hypercholesterolemia, comprising administering to said patient an effective hypocholesterolemic amount of a compound of formula (I), compound of formula (II), compound of formula (III), or compound of formula (IV).

DETAILED DESCRIPTION OF THE INVENTION

As used herein the term "Y" refers to an oxygen atom, a sulfur atom, a sulfinyl group or a sulfonyl group. In other words, the term "Y" refers to a divalent radical of the formula —O—, —S—, —S(O)— or —$SO_2$—. The term "halogen", or "halo" or "Hal" refers to a chlorine, bromine, or iodine atom.

As used herein the terms "A" and "B" refer to $C_1$-$C_{14}$ alkylenes of straight or branched chain configuration. The terms "A" and "B" thus refer to a saturated hydrocarbylene radicals of from 1 to 14 carbon atoms of straight or branched chain configuration. Specifically included within the scope of the terms are the radicals —$CH_2$—, —$CH_2CH_2$—, —$CH_2CH_2CH_2$—, —$CH_2(CH_2)_2CH_2$—, —$CH_2(CH_2)_3CH_2$—, —$CH_2(CH_2)_4CH_2$—, —$CH_2(CH_2)_5CH_2$—, —$CH_2(CH_2)_6CH_2$—, —$CH_2(CH_2)_7CH_2$—, —$CH_2(CH_2)_8CH_2$—, —$CH_2(CH_2)_9CH_2$—, —$CH_2(CH_2)_{10}CH_2$—, —$CH_2(CH_2)_{11}CH_2$—, —$CH_2(CH_2)_{12}CH_2$—, —$CH(CH_3)CH_2$—, —$CH(CH_3)CH_2CH_2$—, —$CH(CH_3)CH_2CH_2CH_2$—, —$CH(CH_3)CH_2(CH_2)_2CH_2$—, —$CH(CH_3)CH_2CH(CH_3)$—, —$CH(CH_3)CH_2CH_2CH(CH_3)$—, —$CH(CH_3)CH_2(CH_2)_2CH(CH_3)$—, and —$CH(CH_3)$—$(CH_2)_3$—$CH(CH_3)$—$(CH_2)_3$—$CH(CH_3)$—$(CH_2)_3$—$CH(CH_3)$—$CH_2$—.

As used herein the term "D" refers to either a $C_1$-$C_4$ saturated or unsaturated alkyl of straight or branched configuration, a group represented by —$CF_3$, $CHF_2$, $CH_2F$ or a phenyl. The term $C_1$-$C_4$ refers to a saturated or unsaturated, branched or straight chained alkyl group containing 1-4 carbon atoms, including —$CH_3$, —$CH_2CH_3$, —$C(CH_3)_3$, —$CH_2CH(CH_3)_2$, or $CH_2$—$CH$=$CH_2$. As used herein the term "E" refers to an oxygen atom or a sulfur atom and the term "$D_1$" refers to a hydrogen, —$CF_3$, $CHF_2$, $CH_2F$ or a phenyl.

It is understood that the compounds of formula (I), (II), (III) and (IV) may exist in a variety of isomeric configurations including geometric as well as stereo isomers. It is further understood that the present invention encompasses all the various isomers depicted by the structures of formulas (I), (II), (III) and (IV) which utilize standard techniques and conventions for designating isomers. The various individual geometric and stereo isomers, as well as mixtures thereof, are included within the scope of the present invention. For example, it is readily apparent that the azadecalinyl ring of the compounds of the present invention bear various substituents which provide a variety of geometric and stereo isomeric configurations. In regard to the bridge-head carbons of the azadecalinyl ring, compounds of the present invention wherein the bridge-head methyl is trans relative to the bridge-head hydrogen are generally preferred. Compounds wherein the non-bridge-head methyl is trans relative to the bridge-head methyl and cis relative to the bridge-head hydrogen are generally preferred. Compounds wherein the hydroxy substituent is cis relative to the bridge-head methyl and trans relative to the bridge-head hydrogen and the non-bridge-head methyl are generally preferred.

The compounds of formula (I) can be prepared by utilizing procedures and techniques well known and appreciated by one of ordinary skill in the art. A general synthetic scheme for preparing these compounds is set forth in Scheme A wherein all substituents, unless otherwise indicated, are previously defined.

Scheme A

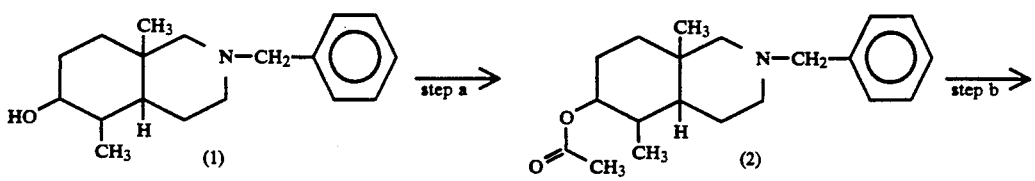

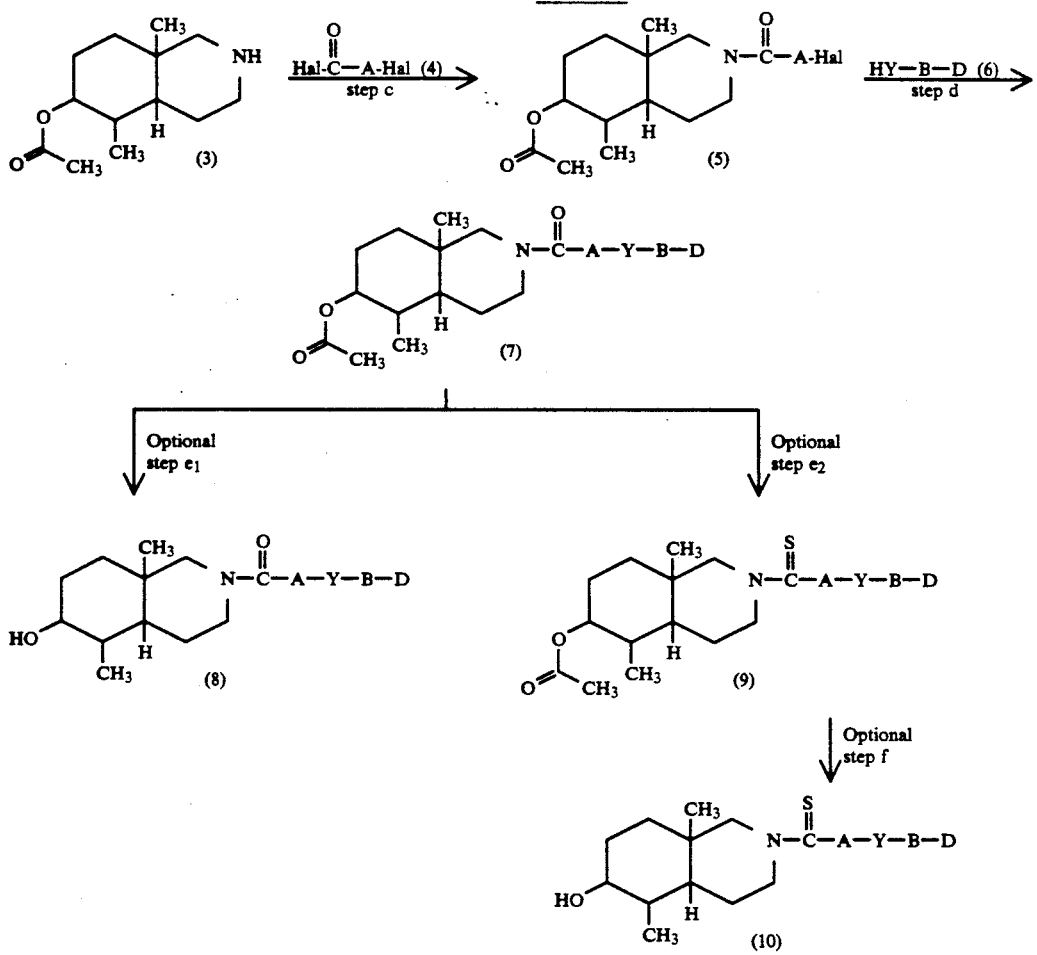

Scheme A provides a general synthetic scheme for preparing compounds of formula (I).

In step a, the 3-alcohol functionality of the appropriate N-benzyl-8-aza-4,10-dimethyl-trans-decal-3-ol (1) is acylated to give the corresponding N-benzyl-8-aza-4,10-dimethyl-decal-3-acetate of structure (2).

For example, the appropriate N-benzyl-8-aza-4,10-dimethyl-trans-decal-3-ol (1) is contacted with a molar excess of an appropriate acylating agent such as acetic anhydride and a molar excess of a suitable non-nucleophilic base, such as pyridine along with a catalytic amount of a acylation catalyst such as dimethylaminopyridine. The reactants are typically stirred together at room temperature for a period of time ranging from 10–60 hours. The N-benzyl-8-aza-4,10-dimethyl-decal-3-acetate of structure (2) is recovered from the reaction zone by extractive methods as is known in the art. It may be purified by silica gel chromatography.

In step b, the N-benzyl functionality of the appropriate N-benzyl-8-aza-4,10-dimethyl-decal-3-acetate of structure (2) is removed to give the corresponding 8-aza-4,10-dimethyl-decal-3-acetate of structure (3).

For example, the appropriate N-benzyl-8-aza-4,10-dimethyl-decal-3-acetate of structure (2) is contacted with a catalytic amount of a hydrogenation catalyst such as 10% palladium/carbon and treated with hydrogen gas at a pressure range of from 40–50 psi. The reactants are typically contacted in a suitable acid solvent such as acetic acid. The reactants are typically shaken together at room temperature for a period of time ranging from 2–24 hours. The 8-aza-4,10-dimethyl-decal-3-acetate of structure (3) is recovered from the reaction zone by extractive methods as is known in the art.

In step c, the amine functionality of the appropriate 8-aza-4,10-dimethyl-decal-3-acetate of structure (3) is alkylated with the appropriate haloalkanoyl chloride of structure (4) to give the corresponding N-(1-oxohaloalkyl)-8-aza-4,10-dimethyl-decal-3-acetate of structure (5).

For example, the appropriate 8-aza-4,10-dimethyl-decal-3-acetate of structure (3) is contacted with a slight molar excess of an appropriate haloalkanoyl chloride of structure (4) and a slight molar excess of a suitable non-nucleophilic base such as triethylamine. The reactants are typically contacted in a suitable organic solvent such as methylene chloride. The reactants are typically stirred together at room temperature for a period of time ranging from 2–24 hours. The N-(1-oxohaloalkyl)-8-aza-4,10-dimethyl-decal-3-acetate of structure (5) is recovered from the reaction zone by extractive methods as is known in the art. It may be purified by silca gel chromatography.

In step d, the N-haloalkanoate functionality of the appropriate N-(1-oxohaloalkyl)-8-aza-4,10-dimethyl-decal-3-acetate of structure (5) is reacted with the appropriate substituted alkyl alcohol or substituted alkyl thiol of structure (6) to give the corresponding N-[(substituted)-(1-oxoalkylhetero)alkyl]-8-aza-4,10-dimethyl-decal-3-acetate of structure (7).

For example, the appropriate N-(1-oxohaloalkyl)-8-aza-4,10-dimethyl-decal-3-acetate of structure (5) is contacted with a molar excess of an appropriate substituted alkyl alcohol or substituted alkyl thiol of structure (6) and a molar excess of a suitable base, such as potassium carbonate. The reactants are typically contacted in a suitable aprotic organic solvent such as dimethylformamide. The reactants are typically stirred together for a period of time ranging from 2–10 hours and at a temperature range of from room temperature to 45° C. The N-[(substituted)-(1-oxoalkylhetero)alkyl]-8-aza-4,10-dimethyl-decal-3-acetate of structure (7) is recovered from the reaction zone by extractive methods as is known in the art. It may be purified by silica gel chromatography.

In optional step $e_1$, the 3-acetate functionality of the appropriate N-[(substituted)-(1-oxoalkylhetero)alkyl]-8-aza-4,10-dimethyl-decal-3-acetate of structure (7) is hydrolyzed to give the corresponding N-[(substituted)-(1-oxoalkylhetero)alkyl]-8-aza-4,10-dimethyl-decal-3-ol of structure (8).

For example, the appropriate N-[(substituted)-(1-oxoalkylhetero)alkyl]-8-aza-4,10-dimethyl-decal-3-acetate of structure (7) is contacted with a molar excess of an appropriate base such as lithium hydroxide or sodium hydroxide. The reactants are typically contacted in a suitable protic organic solvent such as methanol. The reactants are typically stirred together at room temperature for a period of time ranging from 2–24 hours. The N-[(substituted)-(1-oxoalkylhetero)alkyl]-8-aza-4,10-dimethyl-decal-3-ol of structure (8) is recovered from the reaction zone by extractive methods as is known in the art. It may be purified by silica gel chromatography.

In optional step $e_2$, the amide functionality of the appropriate N-[(substituted)-(1-oxoalkylhetero)alkyl]-8-aza-4,10-dimethyl-decal-3-acetate of structure (7) is converted to the corresponding thioamide to give the N-[(substituted)-(1-thioxo)alkylheteroalkyl]-8-aza-4,10-dimethyl-decal-3-acetate of structure (9).

For example, the appropriate N-[(substituted)-(1-oxoalkylhetero)alkyl]-8-aza-4,10-dimethyl-decal-3-acetate of structure (7) is contacted with a slight molar excess of a thioamidating reagent such as Lawesson reagent. The reactants are typically contacted in a suitable organic solvent such as chloroform. The reactants are typically stirred together for a period of time ranging from 2–24 hours and at a temperature range of from room temperature to 60° C. The N-[(substituted)-(1-thioxo)alkylheteroalkyl]-8-aza-4,10-dimethyl-decal-3-acetate of structure (9) is recovered from the reaction zone by evaporation of the solvent. It may be purified by silica gel chromatography.

In optional step f, the 3-acetate functionality of the appropriate N-[(substituted)-(1-thioxo)alkylheteroalkyl]-8-aza-4,10-dimethyl-decal-3-acetate of structure (9) is hydrolyzed to give the corresponding N-[(substituted)-(1-thioxo)alkylheteroalkyl]-8-aza-4,10-dimethyl-decal-3-ol of structure (10) as described previously in optional step $e_1$.

Starting materials for use in Scheme A are readily available to one of ordinary skill in the art. For example, N-benzyl-8-aza-4α,10-dimethyl-trans-decal-3β-ol is described in *Phytochemistry* 24(6) 1223-1232 1985.

The following examples present typical syntheses as described in Scheme A. These examples are understood to be illustrative only and are not intended to limit the scope of the present invention in any way. As used herein, the following terms have the indicated meanings: "g" refers to grams; "mg" refers to milligrams; "mmol" refers to millimoles; "mL" refers to milliliters; "bp" refers to boiling point; "mp" refers to melting point; "°C." refers to degrees Celsius; "mm Hg" refers to millimeters of mercury; "μL" refers to microliters; "μg" refers to micrograms; and "μM" refers to micromolar.

EXAMPLE 1

N-[1-Oxo-5-(3-methylbutylmercapto)pentyl]-8-aza-4α,10-dimethyl-trans-decal-3β-ol Step a:
N-Benzyl-8-aza-4α,10-diemethyl-trans-decal-3β-acetate Mix dimethylaminopyridine (100 mg, 0.82 mmol), pyridine (2 mL, 24.7 mmol) and acetic anhydride (50 mL) and place under a nitrogen atmosphere. Add, by portionwise addition, N-benzyl-8-aza-4α,10-dimethyl-trans-decal-3β-ol (4.5 g, 16.5 mmol) and stir for 48 hours at room temperature. Evaporate the solvent in vacuo, dissolve the residual oil in ethyl ether (250 mL) and wash with 10% sodium hydroxide (2×100 mL). Dry (MgSO$_4$), filter the solution through silica gel and wash with ethyl ether. Evaporate the solvent in vacuo to give the title compound as an oil (5.16 g, 99%).

Anal. Calcd for $C_{20}H_{29}NO_2$: C, 76.15; H, 9.27; N. 4.44; Found: C, 76.28; H, 9.63; N. 4.31.

Step b: 8-Aza-4α,10-dimethyl-trans-decal-3β-acetate

Dissolve N-benzyl-8-aza-4α,10-dimethyl-trans-decal-3β-acetate (4.89 g, 14.6 mmol) in acetic acid (125 mL) and add 10% palladium/carbon (550 mg). Hydrogenate at 50 psi of hydrogen for 15 hours. Filter through celite and azeotrope to dryness to give an off-white solid. Partition between methylene chloride and saturated potassium carbonate, separate the organic phase and wash the aqueous phase with methylene chloride. Dry (MgSO$_4$) the combined organic phases and evaporate the solvent in vacuo to give the title compound.

Step c:
N-(1-Oxo-5-chloropentyl)-8-aza-4α,10-dimethyl-trans-decal-3β-acetate

Dissolve 8-aza-4α,10-dimethyl-trans-decal-3β-acetate (14.6 mmol) in methylene chloride (250 mL), cool to 0° C. and add triethylamine (25 mL, 0.18 mol). Add a solution of 5-chlorovaleryl chloride (2.32 g, 15 mmol) in methylene chloride. Allow to warm to room temperature and let stir overnight. Evaporate the solvent in vacuo, add ethyl ether (200 mL) and wash with 2N hydrochloric acid. Dry (MgSO$_4$), evaporate the solvent in vacuo, purify by silica gel chromatography (50% ethyl acetate/hexane) and wash with 10% sodium hydroxide to give the title compound (49%); MS (CI/CH$_4$) 344 (M+1), 308 (M+1-HCl).

Step d:
N-[1-Oxo-5-(3-methylbutylmercapto)pentyl]-8-aza-4α,10-dimethyl-trans-decal-3β-acetate Mix N-(1-oxo-5-chloropentyl)-8-aza-4α,10-dimethyl-trans-decal-3β-acetate (367 mg, 1.07 mmol), 3-methyl-1-butanethiol (0.4 mL, 3.2 mmol), potassium carbonate (0.67 g, 4.8 mmol) and dimethylformamide (10 mL). Place under nitrogen atmosphere and heat to 40° C. for 2 hours. Partition between ethyl ether (200 mL) and 10% sodium hydroxide (100 mL). Separate the organic phase and extract the aqueous phase with ethyl ether (100 mL). Combine the organic phases and wash with water (4×150 mL) and then brine. Dry (MgSO$_4$) and evaporate the solvent in vacuo. Purify by silica gel chromatography (20%–50% ethyl acetate/hexane) to give the title compound (308 mg).

Optional step e$_1$:
N-[1-Oxo-5-(3-methylbutylmercapto)pentyl]-8-aza-4α,10-dimethyl-trans-decal-3β-ol Dissolve N-[1-oxo-5-(3-methylbutylmercapto)pentyl]-8-aza-4α,10-dimethyl-trans-decal-3β-acetate (250 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo to to give 190 mg of a colorless oil. Purify by silica gel chromatography (5% methanol/methylene chloride) to give the title compound.

Anal. Calcd for $C_{21}H_{39}NO_2S$: C, 68.24; H, 10.64; N, 3.79; Found: C, 68.05; H, 10.70; N, 3.69.

EXAMPLE 2

N-[1-Thioxo-5-(3-methylbutylmercapto)pentyl]-8-aza-4α,10-dimethyl-trans-decal-3β-ol Optional step e$_2$:
N-[1-Thioxo-5-(3-methylbutylmercapto)pentyl]-8-aza-4α,10-dimethyl-trans-decal-3β-acetate Dissolve N-[1-oxo-5-(3-methylbutylmercapto)pentyl]-8-aza-4α,10-dimethyl-trans-decal-3β-acetate (2.63 g, 6.6 mmol) in anhydrous chloroform (50 mL). Add Lawesson reagent (2.83 g, 7 mmol) and stir at 55°–60° C. for several hours. Evaporate the solvent in vacuo and purify by silica gel chromatography to give the title compound.

Optional step f:
N-[1-Thioxo-5-(3-methylbutylmercapto)pentyl]-8-aza-4α,10-dimethyl-trans-decal-3β-ol Dissolve N-[1-thioxo-5-(3-methylbutylmercapto)pentyl]-8-aza-4α,10-dimethyl-trans-decal-3β-acetate (261 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

EXAMPLE 3

N-[1-Oxo-5-(phenylmethylmercapto)pentyl]-8-aza-4α,10-dimethyl-trans-decal-3β-ol

Step d:
N-[1-Oxo-5-(phenylmethylmercapto)pentyl]-8-aza-4α,10-dimethyl-trans-decal-3β-acetate Dissolve N-(1-oxo-5-chloropentyl)-8-aza-4α,10-dimethyl-trans-decal-3β-acetate (351 mg) in dimethylformamide (10 mL) and place under a nitrogen atmosphere. Add potassium carbonate (670 mg,) and benzyl mercaptan (0.36 mL). Heat at 0° C. for 24 hours, patition between 10% sodium hydroxide (75 mL) and ethyl ether (75 mL). Separate the organic phase and extract the aqueous phase with ethyl ether (2×75 mL). Combine the organic phases, dry (MgSO$_4$) and evaporate the solvent in vacuo. Purify by silica gel chromatography (30/70 ethyl acetate/hexane) to give the title compound (334 mg).

Optional step e$_1$:
N-[1-Oxo-5-(phenylmethylmercapto)pentyl]-8-aza-4α,10-dimethyl-trans-decal-3β-ol Dissolve N-[1-oxo-5-(phenylmethylmercapto)pentyl]-8-aza-4α,10-dimethyl-trans-decal-3β-acetate (324 mg) in methanol (2 mL) and place under a nitrogen atmosphere. Add a solution of lithium hydroxide (20 mg in 1 mL of water). Stir at room temperature for 3 hours, dilute with methylene chloride (50 mL) and wash with water. Separate the organic phase and extract the aqueous phase with ethyl ether (2×75 mL). Combine the organic phases, dry (MgSO$_4$) and evaporate the solvent in vacuo. Purify by silica gel chromatography (2% methanol/methylene chloride) to give the title compound.

Anal. Calcd for $C_{23}H_{35}NO_2S$: C, 70.91; H, 9.06; N, 3.60; Found: C, 70.91; H, 8.95; N, 3.57.

EXAMPLE 4

N-[1-Thioxo-5-(phenylmethylmercapto)pentyl]-8-aza-4α,10-dimethyl-trans-decal-3β-ol Optional step e$_2$:
N-[1-Thioxo5-(phenylmethylmercapto)pentyl]-8-aza-4α,10-dimethyl-trans-decal-3β-acetate Dissolve N-[1-oxo-5-(phenylmethylmercapto)pentyl]-8-aza-4α,10-dimethyl-trans-decal-3β-acetate (2.77 g, 6.6 mmol) in anhydrous chloroform (50 mL). Add Lawesson reagent (2.83 g, 7 mmol) and stir at 55-60° C. for several hours. Evaporate the solvent in vacuo and purify by silica gel chromatography to give the title compound.

Optional step f:
N-[1-Thioxo-5-(phenylmethylmercapto)pentyl]-8-aza-4α,10-dimethyl-trans-decal-3β-ol Dissolve N-[1-thioxo-5-(phenylmethylmercapto)pentyl]-8-aza-4α,10-dimethyl-trans-decal-3β-acetate (274 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

The following compounds can be prepared analogously to those described in Examples 1–4:
N-[1-Thioxo-5-(phenylmethylsulfinyl)pentyl]-8-aza-4α,10-dimethyl-trans-decal-3β-ol;
N-[1-Oxo-5-(phenylmethylsulfinyl)pentyl]-8-aza-4α,10-dimethyl-trans-decal-3β-ol;
N-[1-Oxo-5-(3-methylbutylsulfinyl)pentyl]-8-aza-4α,10-dimethyl-trans-decal-3β-ol;
N-[1-Thioxo-5-(3-methylbutylsulfinyl)pentyl]-8-aza-4α,10-dimethyl-trans-decal-3β-ol.

N-[1-Thioxo-5-(phenylmethylsulfonyl)pentyl]-8-aza-4α,10-dimethyl-trans-decal-3β-ol;

N-[1-Oxo-5-(phenylmethylsulfonyl)pentyl]-8-aza-4α,10-dimethyl-trans-decal-3β-ol;

N-[1-Oxo-5-(3-methylbutylsulfonyl)pentyl]-8-aza-4α,10-dimethyl-trans-decal-3β-ol;

N-[1-Thioxo-5-(3-methylbutylsulfonyl)pentyl]-8-aza-4α,10-dimethyl-trans-decal-3β-ol.

The compounds of formula (II) can be prepared by utilizing procedures and techniques well known and appreciated by one of ordinary skill in the art. A general synthetic scheme for preparing these compounds is set forth in Scheme B wherein all substituents, unless otherwise indicated, are previously defined.

dimethyl-decal-3-acetate of structure (14) as described previously in Scheme A, optional step $e_2$.

In optional step c, the 3-acetate functionality of the appropriate N-[(substituted)-(1-thicarbonyl)heteroalkyl]-8-aza-4,10-dimethyl-decal-3-acetate of structure (14) is hydrolyzed to give the corresponding N-[(substituted)-(1-thicarbonyl)heteroalkyl]-8-aza-4,10-dimethyl-decal-3-ol of structure (15) as described previously in Scheme A, optional step f.

Starting materials for use in Scheme B are readily available to one of ordinary skill in the art.

The following examples present typical syntheses as described in Scheme B. These examples are understood to be illustrative only and are not intended to limit the

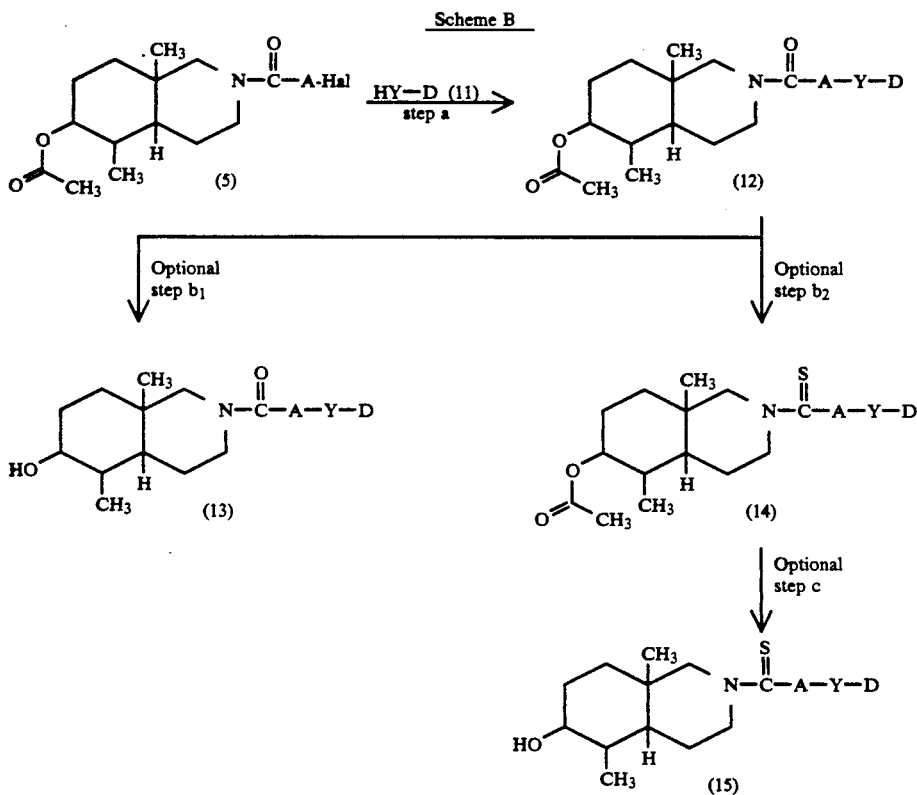

Scheme B

Scheme B provides a general synthetic scheme for preparing compounds of formula (II).

In step a, the N-haloalkanoate funtionality of the appropriate N-(1-oxohaloalkyl)-8-aza-4,10-dimethyl-decal-3-acetate of structure (5) is reacted with the appropriate substituted alcohol or substituted thiol of structure (11) to give the corresponding N-[(substituted)-(1-oxo)heteroalkyl]-8-aza-4,10-dimethyl-decal-3-acetate of structure (12) as described previously in Scheme A, step d.

In optional step $b_1$, the 3-acetate functionality of the appropriate N-[(substituted)-(1-oxo)heteroalkyl]-8-aza-4,10-dimethyl-decal-3-acetate of structure (12) is hydrolyzed to give the corresponding N-[(substituted)-(1-oxo)heteroalkyl]-8-aza-4,10-dimethyl-decal-3-ol of structure (13) as described previously in Scheme A, optional step $e_1$.

In optional step $b_2$, the amide functionality of the appropriate N-[(substituted)-(1-oxo)heteroalkyl]-8-aza-4,10-dimethyl-decal-3-acetate of structure (12) is converted to the corresponding thioamide to give the N-[(substituted)-(1-thicarbonyl)heteroalkyl]-8-aza-4,10- scope of the present invention in any way.

EXAMPLE 5

N-[1-Oxo-5-(phenylmercapto)pentyl]-8-aza-4α,10-dimethyl-trans-decal-3β-ol

Step a:
N-[1-Oxo-5-(phenylmercapto)pentyl]-8-aza-4α,10-dimethyl-trans-decal-3β-acetate Dissolve N-(1-oxo-5-chloropentyl)-8-aza-4α,10-dimethyl-trans-decal-3β-acetate (358 mg) in dimethylformamide (10 mL) and place under a nitrogen atmosphere. Add potassium carbonate (0.7 g) and thiophenol (0.33 mL). Heat at 45° C. for 5 hours, partition between 10% sodium hydroxide (150 mL) and methylene chloride (200 mL). Separate the organic phase and extract the aqueous phase with methylene chloride (3×200 mL). Combine the organic phases and evaporate the solvent in vacuo. Dissolve the residue in ethyl ether and wash with water (3×200 mL). Dry (MgSO₄) and evaporate the solvent in vacuo to give 530 mg of a colorless oil. Purify by silica gel chromatography (10%–50% ethyl acetate/hexane) to give the title compound (480 mg).

Optional step $b_1$:
N-[1-Oxo-5-(phenylmercapto)pentyl]-8-aza-4α,10-dimethyl-trans-decal-3β-ol Dissolve N-[1-oxo-5-(phenylmercapto)pentyl]-8-aza-4α,10-dimethyl-trans-decal-3β-acetate (480 mg) in methanol (3 mL) and place under a nitrogen atmosphere. Add lithium hydroxide (0.3 g in 1 mL of water) and stir overnight. Dilute with methylene chloride (50 mL) and wash with water. Separate the organic phase and extract the aqueous phase with ethyl ether (2×50 mL). Combine the organic phases and wash with brine. Dissolve the residue in ethyl ether and with water (3×200 mL). Dry (MgSO$_4$) and evaporate the solvent in vacuo to give the title compound.

Anal. Calcd for C$_{22}$H$_{33}$NO$_2$S: C, 70.36; H, 8.86; N, 3.73; Found: C, 70.22; H, 9.01; N, 3.66.

EXAMPLE 6

N-[1-Thioxo-5-(phenylmercapto)pentyl]-8-aza-4α,10-dimethyl-trans-decal-3β-ol

Optional Step $b_2$:
N-[1-Thioxo-5-(phenylmercacto)pentyl]-8-aza-4α,10-dimethyl-trans-decal-3β-acetate Dissolve N-[1-oxo-5-(phenylmercapto)pentyl]-8-aza-4α,10-dimethyl-trans-decal-3β-acetate (2.67 g, 6.6 mmol) in anhydrous chloroform (50 mL). Add Lawesson reagent (2.83 g, 7 mmol) and stir at 55°–60° C. for several hours. Evaporate the solvent in vacuo and purify by silica gel chromatography to give the title compound.

Optional step c:
N-[1-Thioxo-5-(phenylmercapto)pentyl]-8-aza-4α,10-dimethyl-trans-decal-3β-ol Dissolve N-[1-thioxo-5-(phenylmercapto)pentyl]-8-aza-4α,10-dimethyl-trans-decal-3β-acetate (265 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

EXAMPLE 7

N-[1-Oxo-5-(2-propenemercapto)pentyl]-8-aza-4α,10-dimethyl-trans-decal-3β-ol

Step a:
N-[1-Oxo-5-(2-propenemercapto)pentyl]-8-aza-4α,10-dimethyl-trans-decal-3β-acetate Dissolve N-(1-oxo-5-chloropentyl)-8-aza-4α,10-dimethyl-trans-decal-3β-acetate (265 mg) in dimethylformamide (10 mL) and place under a nitrogen atmosphere. Add potassium carbonate (0.51 g) and allyl mercaptan (0.24 mL). Heat at 65° C. for 3 hours and partition between 10% sodium hydroxide (100 mL) and ethyl ether (100 mL). Separate the organic phase and extract the aqueous phase with ethyl ether (2×100 mL). Combine the organic phases, dry (MgSO$_4$) and evaporate the solvent in vacuo. Purify by silica gel chromatography to give the title compound.

Optional step $b_1$:
N-[1-Oxo-5-(2-propenemercapto)pentyl]-8-aza-4α,10-dimethyl-trans-decal-3β-ol Dissolve N-[1-oxo-5-(2-propenemercapto)pentyl]-8-aza-4α,10-dimethyl-trans-decal-3β-acetate (220 mg) in methanol (2.5 mL) and add lithium hydroxide (15 mg in 0.5 mL of water). Stir at room temperature overnight. Dilute with methylene chloride (50 mL) and wash with water. Separate the organic phase and extract the aqueous phase with methylene chloride (2×50 mL). Combine the organic phases, dry (Na$_2$SO$_4$) and evaporate the solvent in vacuo. Purify by silica gel chromatography (2–5% methanol in methylene chloride) to give the title compound (108 mg).

EXAMPLE 8

N-[1-Thioxo-5-(2-propenemercapto)pentyl]-8-aza-4α,10-dimethyl-trans-decal-3β-ol

Optional step $b_2$:
N-[1-Thioxo-5-(2-propenemercapto)pentyl]-8-aza-4α,10-dimethyl-trans-decal-3β-acetate Dissolve N-[1-oxo-5-(2-propenemercapto)pentyl]-8-aza-4α,10-dimethyl-trans-decal-3β-acetate (2.44 g, 6.6 mmol) in anhydrous chloroform (50 mL). Add Lawesson reagent (2.83 g, mmol) and stir at 55°–60° C. for several hours. Evaporate the solvent in vacuo and purify by silica gel chromatography to give the title compound.

Optional step c:
N-[1-Thioxo-5-(2-propenemercapto)pentyl]-8-aza-4α,10-dimethyl-trans-decal-3β-ol Dissolve N-[1-thioxo-5-(2-propenemercapto)-pentyl]-8-aza-4α,10-dimethyl-trans-decal-3β-acetate (243 mg, 0.63 mmol) in methanol (2 mL) and add a solution of lithium hydroxide (lmmol in lmL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

The following compounds can be prepared analogously to those described in Examples 5–8:
N-[1-Oxo-10-(methoxy)decyl]-8-aza-4α,10-dimethyl-trans-decal-3β-ol;
N-[1-Thioxo-10-(methoxy)decyl]-8-aza-4α,10-dimethyl-trans-decal-3β-ol.

The compounds of formula (III) can be prepared by utilizing procedures and techniques well known and appreciated by one of ordinary skill in the art. A general synthetic scheme for preparing these compounds is set forth in Scheme C wherein all substituents, unless otherwise indicated, are previously defined.

Scheme C

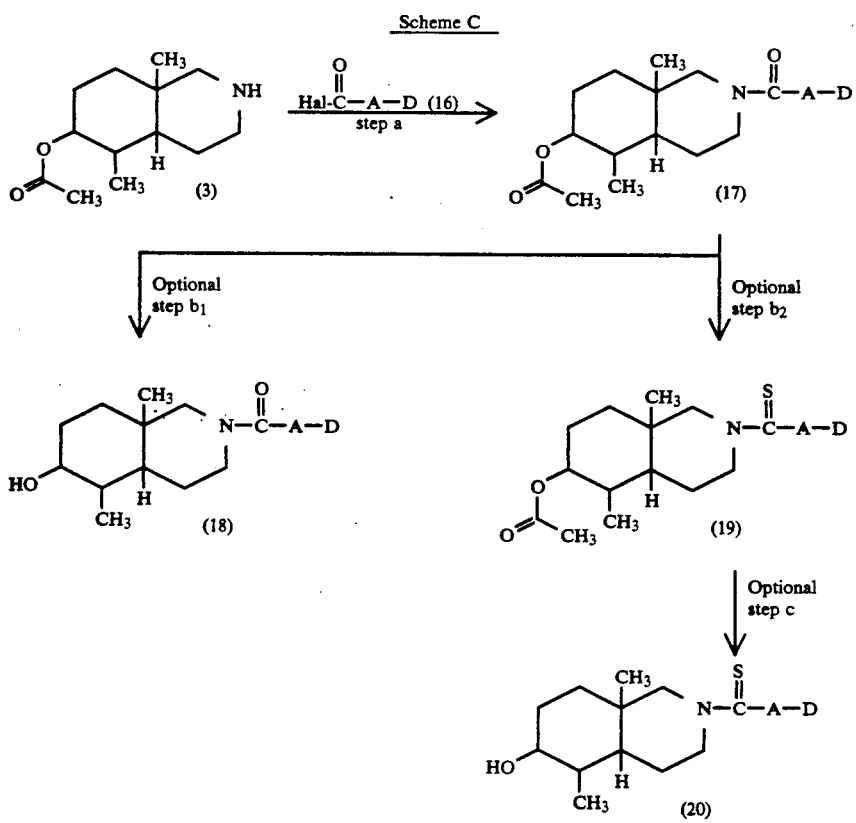

Scheme C provides a general synthetic scheme for preparing compounds of formula (III).

In step a, the amine functionality of the appropriate 8-aza-4,10-dimethyl-decal-3-acetate of structure (3) is alkylated with the appropriate substituted alkanoyl chloride of structure (16) to give the corresponding N-[(substituted)-1-oxoalkyl]-8-aza-4,10-dimethyl-decal-3-acetate of structure (17) as described previously in Scheme A, step c.

In optional step $b_1$, the 3-acetate functionality of the appropriate N-[(substituted)-1-oxoalkyl]-8-aza-4,10-dimethyl-decal-3-acetate of structure (17) is hydrolyzed to give the corresponding N-[(substituted)-1-oxoalkyl]-8-aza-4,10-dimethyl-decal-3-ol of structure (18) as described previously in Scheme A, optional step $e_1$.

In optional step $b_2$, the amide functionality of the appropriate N-[(substituted)-1-oxoalkyl]-8-aza-4,10-dimethyl-decal-3-acetate of structure (17) is converted to the corresponding thioamide to give the N-[(substituted)-1-(thioxo)alkyl]-8-aza-4,10-dimethyl-decal-3-acetate of structure (19) as described previously in Scheme A, optional step $e_2$.

In optional step c, the 3-acetate functionality of the appropriate N-[(substituted)-1-(thioxo)alkyl]-8-aza-4,10-dimethyl-decal-3-acetate of structure (19) is hydrolyzed to give the N-[(substituted)-1-(thioxo)alkyl]-8-aza-4,10-dimethyl-decal-3-ol of structure (20) as described previously in Scheme A, optional step f.

Starting materials for use in Scheme C are readily available to one of ordinary skill in the art.

The following examples present typical syntheses as described in Scheme C. These examples are understood to be illustrative only and are not intended to limit the scope of the present invention in any way.

EXAMPLE 9

N-(1-Oxododecyl)-8-aza-4α,10-dimethyl-trans-decal-3β-ol

Step a:
N-(1-Oxododecyl)-8-aza-4α,10-dimethyl-trans-decal-3β-acetate

Dissolve lauric acid (192 mg, 0.96 mmol) in methylene chloride (5 mL) and add dimethylformamide (3 drops). Add oxalyl chloride (85 μL, 0.96 mmol) and stir until evolution of carbon dioxide is complete to give lauryol chloride.

Dissolve 8-aza-4α,10-dimethyl-trans-decal-3β-acetate (197 mg, 0.87 mmol) in methylene chloride (5 mL) and add triethylamine (2 mL). Add the solution of lauryol chloride (0.96 mmol) and stir at room temperature for 2 hours. Evaporate the solvent in vacuo and add ethyl ether (100 mL). Extract with 10% sodium hydroxide, dry (MgSO$_4$) and filter through silica gel using ethyl ether as the eluent. Evaporate the solvent in vacuo to give 290 mg of an orange oil. Purify by silica gel chromatography (30% ethyl acetate/hexane) to give the title compound (172 mg).

Optional step $b_1$:
N-(1-Oxododecyl)-8-aza-4α,10-dimethyl-trans-decal-3β-ol

Dissolve N-(1-oxododecyl)-8-aza-4α,10-dimethyl-trans-decal-3β-acetate (172 mg, 0.42 mmol) in methanol (5 mL). Add 2 sodium spheres and stir until the sodium dissolves. Stir at room temperature for 2 hours and evaporate the solvent in vacuo. Add ethyl ether (100 mL), wash with water and dry (MgSO$_4$). Evaporate the solvent in vacuo to give the title compound as a viscous oil (129 mg).

Anal. Calcd for $C_{23}H_{43}NO_2$: C, 75.56; H, 11.86; N, 3.83; Found: C, 75.44; H, 11.95; N, 3.69.

EXAMPLE 10

N-(1-Thioxododecyl)-8-aza-4α,10-dimethyl-trans-decal-3β-ol

Optional step b$_2$:
N-(1-Thioxododecyl)-8-aza-4α,10-dimethyl-trans-decal-3β-acetate Dissolve N-(1-oxododecyl)-8-aza-4α,10-dimethyl-trans-decal-3β-acetate (2.61 g, 6.6 mmol) in anhydrous chloroform (50 mL). Add Lawesson reagent (2.83 g, 7 mmol) and stir at 55°–60° C. for several hours. Evaporate the solvent in vacuo and purify by silica gel chromatography to give the title compound.

Optional step c:
N-(1-Thioxododecyl)-8-aza-4α,10-dimethyl-trans-decal-3β-ol

Dissolve N-(1-thioxododecyl)-8-aza-4α,10-dimethyl-trans-decal-3β-acetate (259 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

EXAMPLE 11

N-[1-Oxo-12,12,12-trifluorododecyl]-8-aza-4α,10-dimethyl-trans-decal-3β-ol

Step a:
N-[1-Oxo-12,12,12-trifluorododecyl]-8-aza-4α,10-dimethyl-trans-decal-3β-acetate Place oxalyl chloride (0.5 mL of a 2M solution in methylene chloride, 1 mmol) under an argon atmosphere and cool with a dry ice/acetone bath. Add dimethylsulfoxide (0.14 mL, 2 mmol) and stir for 10 minutes at −70° C. Add 4,4,4-trifluorobutanol (110 mg, 0.86 mmol) in methylene chloride (1 mL). Stir for 20 minutes at −78° C. Add triethylamine (0.56 mL, 4 mmol), remove the cooling bath and stir for 45 minutes. Purify by silica gel chromatography to give 4,4,4-trifluorobutanal.

Dissolve 8-bromooctanoic acid (1.0 g) in anhydrous toluene (3 mL) and add triphenylphosphine (1.21 g). Heat to reflux overnight. Separate the lower phase crystallize (ethanol/ethyl ether) to give (8-carboxyoctyl)triphenylphosphonium bromide (1.0 g).

Dissolve (8-carboxyoctyl)triphenylphosphonium bromide (709 mg, 1.46 mmol) in anhydrous tetrahydrofuran (25 mL), cool to −78° C. and place under a nitrogen atmosphere. Add lithium diisopropylamide (2.0 mL of a 1.5M solution in tetrahydrofuran, 3.0 mmol) and stir at −78° C. until anion formation is complete. Add a solution of 4,4,4-trifluorobutanal (181 mg, 1.46 mmol) in anhydrous tetrahydrofuran (25 mL). Stir at −78° C. for several hours, then allow to warm to room temperature overnight. Quench carefully with saturated ammonium chloride and evaporate the volatiles in vacuo. Partition the residue between ethyl acetate and brine and separate the organic phase. Extract the aqueous phase with ethyl acetate (2×50 mL) and combine the organic phases. Dry (MgSO$_4$) and evaporate the solvent in vacuo. Purify by silica gel chromatography to give 12,12,12-trifluoro-8-dodecenoic acid.

Dissolve 12,12,12-trifluoro-8-dodecenoic acid (1.39 g, 5.5 mmol) in ethanol (50 mL) and place in a Paar hydrogenation flask. Add 10% palladium/carbon (500 mg). Charge the vessel to 50 psi and shake for 18 hours. Filter through celite and remove the solvent in vacuo to give 12,12,12-trifluorododecanoic acid.

Dissolve 12,12,12-trifluorododecanoic acid (244 mg, 0.96 mmol) in methylene chloride (5 mL) and add dimethylformamide (3 drops). Add oxalyl chloride (85 μL, 0.96 mmol) and stir until evolution of carbon dioxide is complete to give 12,12,12-trifluorododecanoyl chloride.

Dissolve 8-aza-4α,10-dimethyl-trans-decal-3β-acetate (197 mg, 0.87 mmol) in methylene chloride (5 mL) and add triethylamine (2 mL). Add the solution of 12,12,12-trifluorododecanoyl chloride (262 mg, 0.96 mmol) and stir at room temperature for 2 hours. Evaporate the solvent in vacuo and add ethyl ether (100 mL). Extract with 10% sodium hydroxide, dry (MgSO$_4$) and filter through silica gel using ethyl ether as the eluent. Evaporate the solvent in vacuo and purify by silica gel chromatography to give the title compound.

Optional step b$_1$: N-[1-Oxo-12,12,12-trifluorododecyl]-8-aza-4α,10-dimethyl-trans-decal-3β-ol Dissolve N-[1-oxo-12-(3,3,3-trifluoro)dodecyl]-8-aza-4α,10-dimethyl-trans-decal-3β-acetate (283 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

EXAMPLE 12

N-[1-Thioxo-12,12,12-trifluorododecyl]-8-aza-4α,10-dimethyl-trans-decal-3β-ol

Optional step b$_2$:
N-[1-Thioxo-12,12,12-trifluorododecyl]-8-aza-4α,10-dimethyl-trans-decal-3β-acetate Dissolve N-[1-oxo-12,12,12-trifluorododecyl]-8-aza-4α,10-dimethyl-trans-decal-3β-acetate (2.96 g, 6.6 mmol) in anhydrous chloroform (50 mL). Add Lawesson reagent (2.83 g, 7 mmol) and stir at 55°–60° C. for several hours. Evaporate the solvent in vacuo and purify by silica gel chromatography to give the title compound.

Optional step c:
N-[1-Thioxo-12,12,12-trifluorododecyl]-8-aza-4α,10-dimethyl-trans-decal-3β-ol Dissolve N-[1-thioxo-12,12,12-trifluorododecyl]-8-aza-4α,10-dimethyl-trans-decal-3β-acetate (293 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

EXAMPLE 13

N-(1-Oxododecyl)-8-aza-4α,10-dimethyl-trans-decal-3α-ol

Step a:
N-(1-Oxododecyl)-8-aza-4α,10-dimethyl-trans-decal-3α-acetate

Mix N-benzyl-8-aza-4α,10-dimethyl-trans-decal-3β-ol (550 mg, 2.01 mmol), triphenylphosphine (551 mg, 2.1 mmol), acetic acid (2.5 mmol) and ethyl ether (50 mL). Place under an argon atmosphere, add diethylazodicarboxylate (330 μL, 2.1 mmol) and stir at room temperature overnight. Dilute with ethyl ether and wash several times with 2N sodium hydroxide. Dry (MgSO$_4$), evaporate the solvent in vacuo and purify by silica gel chromatography (20% ethyl acetate/hexane) to give N-benzyl-8-aza-4α,10-dimethyl-trans-decal-3α-acetate.

Dissolve N-benzyl-8-aza-4α,10-dimethyl-trans-decal-3α-acetate (4.89 g, 14.6 mmol) in acetic acid (125 mL) and treat with 10% palladium/carbon (550 mg). Hydrogenate at 50 psi of hydrogen for 15 hours. Filter through celite and azeotrope to dryness to give 8-aza-4α,10-dimethyl-trans-decal-3α-acetate.

Dissolve 8-aza-4α,10-dimethyl-trans-decal-3α-acetate (197 mg, 0.87 mmol) in methylene chloride (5 mL) and add triethylamine (2 mL). Add the solution of lauryol chloride (0.96 mmol) and stir at room temperature for 2 hours. Evaporate the solvent in vacuo and add ethyl ether (100 mL). Extract with 10% sodium hydroxide, dry (MgSO$_4$) and filter through silica gel using ethyl ether as the eluent. Evaporate the solvent in vacuo and purify by silica gel chromatography to give the title compound.

Optional step b$_1$: N-(1-Oxododecyl)-8-aza-4α,10-dimethyl-trans-decal-3α-ol

Dissolve N-(1-oxododecyl)-8-aza-4α,10-dimethyl-trans-decal-3α-acetate (258 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

EXAMPLE 14

N-(1-Thioxododecyl)-8-aza-4α,10-dimethyl-trans-decal-3α-ol

Optional step b$_2$:
N-(1-Thioxododecyl)-8-aza-4α,10-dimethyl-trans-decal-3α-acetate Dissolve N-(1-oxododecyl)-8-aza-4α,10-dimethyl-trans-decal-3α-acetate (2.70 g, 6.6 mmol) in anhydrous chloroform (50 mL). Add Lawesson reagent (2.83 g, 7 mmol) and stir at 55°-60° C. for several hours. Evaporate the solvent in vacuo and purify by silica gel chromatography to give the title compound.

Optional step c:
N-(1-Thioxododecyl)-8-aza-4α,10-dimethyl-trans-decal-3α-ol

Dissolve N-(1-thioxododecyl)-8-aza-4α,10-dimethyl-trans-decal-3α-acetate (268 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

EXAMPLE 15

N-(1-Oxo-8-phenyloctyl)-8-aza-4α,10-dimethyl-trans-decal-3β-ol

Step a:
N-(1-Oxo-8-phenyloctyl)-8-aza-4α,10-dimethyl-trans-decal-3α-acetate

Mix 8-phenyloctanoic acid (162 mg), one drop of dimethylformamide and methylene chloride (5 mL). Place under nitrogen atmosphere and add oxalyl chloride (0.07 mL). Stir at room temperature for 2 hours and add to a solution of 8-aza-4α,10-dimethyl-trans-decal-3α-acetate (150 mg) and trifluoroacetic acid (1.5 mL) in methylene chloride (5 mL). Stir at room temperature overnight. Quench with a small amount of methanol, partition between ethyl ether (200 mL) and 10% hydrochloric acid (100 mL). Separate the organic phase and wash with hydrochloric acid (200 mL) then with saturated sodium hydrogen carbonate. Dry (Na$_2$SO$_4$) and evaporate the solvent in vacuo to give 300 mg of a yellow oil. Purify by silica gel chromatography (20-50% ethyl acetate/hexane) to give the title compound as a colorless oil (200 mg, 70%).

Optional step b$_1$: N-(1-Oxo-8-phenyloctyl)-8-aza-4α,10-dimethyl-trans-decal-3α-ol Dissolve N-(1-oxo-8-phenyloctyl)-8-aza-4α,10-dimethyl-trans-decal-3α-acetate (200 mg, 0.468 mmol) in methanol (4 mL) and add a solution of lithium hydroxide (0.5 mL of a 1M solution). Stir at room temperature under a nitrogen atmosphere for 24 hours. Partition between water (200 mL) and methylene chloride (200 mL). Separate the organic phase and extract the aqueous phase with methylene chloride (2×100 mL). Combine the organic phases, dry (Na$_2$SO$_4$) and evaporate the solvent in vacuo. Purify by silica gel chromatography (1:1 ethyl acetate/hexane) to give the title compound (153 mg).

The following compounds can be prepared analogously to those described in Examples 13-15:

N-[1-Thioxo-11,11-dimethyldodecyl]-8-aza-4α,10-dimethyl-trans-decal-3β-ol;

N-[1-Oxo-11,11-dimethyldodecyl]-8-aza-4α,10-dimethyl-trans-decal-3β-ol;

N-(1-Thioxo-8-phenyloctyl)-8-aza-4α,10-dimethyl-trans-decal-3β-ol.

The compounds of formula (IV) can be prepared by utilizing procedures and techniques well known and appreciated by one of ordinary skill in the art. A general synthetic scheme for preparing these compounds is set forth in Scheme D wherein all substituents, unless otherwise indicated, are previously defined.

Scheme D

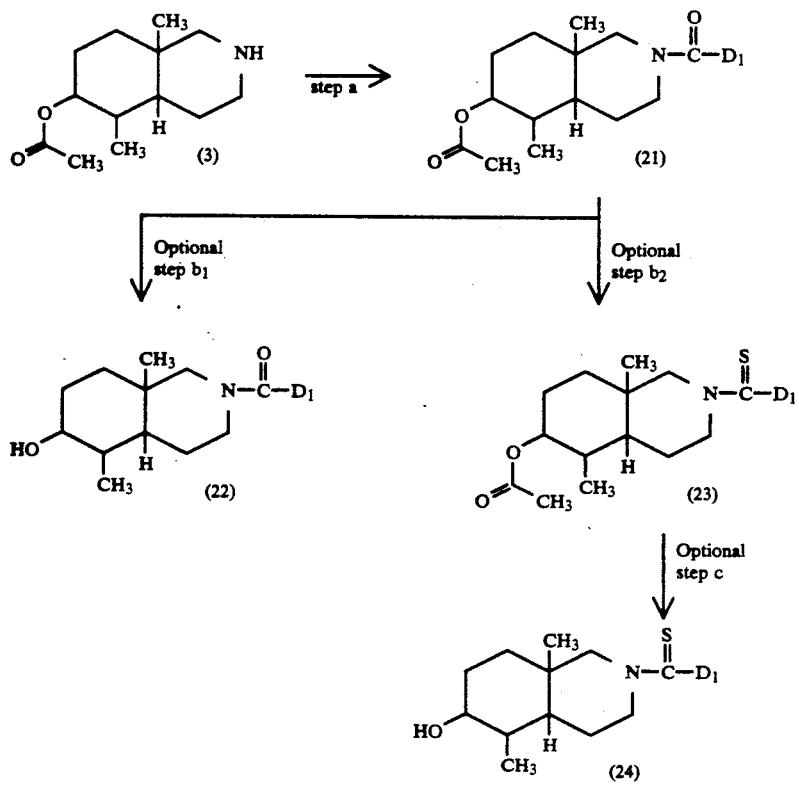

Scheme D provides a general synthetic scheme for preparing compounds of formula (IV).

In step a, the amine functionality of the appropriate 8-aza-4,10-dimethyl-decal-3-acetate of structure (3) is either acylated or formylated to give the corresponding N-(1-oxoalkyl)-8-aza-4,10-dimethyl-decal-3-acetate of structure (21) or the corresponding N-formyl-8-aza-4,10-dimethyl-decal-3-acetate of structure (21).

For example, the appropriate 8-aza-4,10-dimethyl-decal-3-acetate of structure (3) can be acylated with an appropriate acylating agent such as acetyl chloride or acetic anhydride to give the corresponding N-(1-oxoalkyl)-8-aza-4,10-dimethyl-decal-3-acetate of structure (21) as described previously in Scheme A, step c.

Alternatively, the appropriate 8-aza-4,10-dimethyl-decal-3-acetate of structure (3) can be contacted with a molar excess of a silylating agent such as t-butyldimethylsilyl chloride, a catalytic amount of an acylating catalyst, such as dimethyaminopyridine, a molar excess of a non-nucleophilic base, such as triethylamine and a molar excess of a formylating agent such as dimethylformamide. The reactants are typically stirred together for a period of time ranging from 2-24 hours and at a temperature range of from room temperature to 40° C. The N-formyl-8-aza-4,10-dimethyl-decal-3-acetate of structure (21) is recovered from the reaction zone by first hydrolyzing with an acid, such as dilute hydrochloric acid, followed by extractive methods as is known in the art.

In optional step $b_1$, the 3-acetate functionality of the appropriate N-(1-oxoalkyl)-8-aza-4,10-dimethyl-decal-3-acetate of structure (21) or N-formyl-8-aza-4,10-dimethyl-decal-3-acetate of structure (21) is hydrolyzed to give the corresponding N-(1-oxoalkyl)-8-aza-4,10-dimethyl-decal-3-ol of structure (22) or N-formyl-8-aza-4,10-dimethyl-decal-3-ol of structure (22) as described previously in Scheme A, optional step $e_1$.

In optional step $b_2$, the amide functionality of the appropriate N-(1-oxoalkyl)-8-aza-4,10-dimethyl-decal-3-ol of structure (22) or N-formyl-8-aza-4,10-dimethyl-decal-3-ol of structure (22) is converted to the corresponding thioamide the give the N-[(1-thioxo)alkyl]-8-aza-4,10-dimethyl-decal-dimethyl-decal-3-acetate of structure (23) or N-thioformate-8-aza-4,10-dimethyl-decal-3-ol of structure (24) or N-thioformate-8-aza-4,10-dimethyl-decal-3-l of structure (24) as described previously in Scheme A, optional step $e_2$.

In optional step c, the 3-acetate functionality of the appropriate N-[(1-thioxo)alkyl]-8-aza-4,10-dimethyl-decal-3-acetate of structure (23) or N-thioformate-8-aza-4,10-dimethyl-decal-3-acetate of structure (24) is hydrolyzed to give the corresponding N-[(1-thioxo)alkyl]-8-aza-4,10-dimethyl-decal-3-ol of structure (24) or N-thioformate-8-aza-4,10-dimethyl-decal-3-ol of structure (24) as described previously in Scheme A, optional step f.

Starting materials for use in Scheme D are readily available to one of ordinary skill in the art.

The following examples present typical syntheses as described in Scheme D. These examples are understood to be illustrative only and are not intended to limit the scope of the present invention in any way.

EXAMPLE 16

N-(1-Oxoethyl)-8-aza-4α,10-dimethyl-trans-decal-3β-ol

Step a:
N-(1-Oxoethyl)-8-aza-4α,10-dimethyl-trans-decal-3β-acetate

Dissolve 8-aza-4α,10-dimethyl-trans-decal-3β-acetate (197 mg, 0.87 mmol) in methylene chloride (5 mL) and add triethylamine (2 mL). Add the solution of acetyl chloride (0.96 mmol) and stir at room temperature for 2 hours. Evaporate the solvent in vacuo and add ethyl ether (100 mL). Extract with 10% sodium hydroxide, dry (MgSO$_4$) and filter through silica gel using ethyl ether as the eluent. Evaporate the solvent in vacuo and purify by silica gel chromatography to give the title compound.

Optional step b$_1$:
N-(1-Oxoethyl)-8-aza-4α,10-dimethyl-trans-decal-3β-ol

Dissolve N-(1-oxoethyl)-8-aza-4α,10-dimethyl-trans-decal-3β-acetate (168 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

Anal. Calcd for C$_{13}$H$_{23}$NO$_2$: C, 69,30; H, 10.29; N, 6.22; Found: C, 69.07; H, 10.58; N, 6.05.

EXAMPLE 17

Step a:
N-Formyl-8-aza-4α,10-dimethyl-trans-decal-3β-acetate

Mix 8-aza-4α,10-dimethyl-trans-decal-3β-acetate (1.25 g, 5.5 mmol), t-butyl-dimethylsilyl chloride (1.64 g, 11 mmol), dimethylaminopyridine (0.1 g), dimethylformamide (25 mL) and triethylamine (5 mL). Heat at 40° C. for several hours, dilute with ethyl ether, wash with water (3×), 2N hydrochloric acid, water, and brine. Dry (MgSO$_4$), evaporate the solvent in vacuo and purify by silica gel chromatography to give the title compound.

Optional step b$_1$:
N-Formyl-8-aza-4α,10-dimethyl-trans-decal-3β-ol

Dissolve N-formyl-8-aza-4α,10-dimethyl-trans-decal-3β-acetate (159 mg, 0.63 mmol) in methanol (2 mL) and add a solution of lithium hydroxide (1 mmol in 1 mL of water). Stir at room temperature under a nitrogen atmosphere for 24 hours. Dilute with methylene chloride (50 mL) and wash with water. Separate the organic phase and extract the aqueous phase with methylene chloride (2×50 mL). Combine the organic phases and wash with brine. Dry (MgSO$_4$) and evaporate the solvent in vacuo and purify by silica gel chromatography to give the title compound.

The following compound can be prepared analogously to described in Examples 16–18:
N-(1-Oxotrifluoroethyl)-8-aza-4α,10-dimethyl-trans-decal-3β-ol.

The following example illustrates the utility of compounds of formula (I), (II), (III), or (IV) in inhibiting cholesterol biosynthesis. This example is understood to be illustrative only and is not intended to limit the scope of the present invention in any way.

EXAMPLE 18

Inhibition of Oxidosqualene Cyclase

1. Inhibition of Oxidosqualene Cyclase in HepG2 Cells (IC$_{50}$)

HepG2 cells, obtained from American Type Culture Collection, are seeded into plastic 6-well multiwell dishes and grown to 60–70% confluency in an atmosphere of 5%CO$_2$ at 37° C. using Minimal Essential Media supplemented with 10% fetal bovine serum as culture media. The cells are washed and the media is replaced with one containing 10% lipoprotein-deficient serum instead of 10% fetal bovine serum. Twenty-four hours later the test compound is added to the culture media in ethanol to obtain concentrations of between 0 and 100 μM. One hour after the addition of the test compound, 2.0 μC of [$^{14}$C]acetate is added to each well and the cells are allowed to incubate for an additional 2–3 hours. The cells are then harvested and extracted for analysis of $^{14}$C-labeled cholesterol, squalene monoepoxide and squalene diepoxide. These metabolites are separated and identified by a combination of high performance liquid chromatography and flow-through liquid scintillation Spectroscopy. An IC$_{50}$ for the inhibition of [$^{14}$C]cholesterol biosynthesis is calculated based on the radioactivity in controls and treated cells.

2. Inhibition of Purified Oxidosqualene Cyclase (I$_{10}$)

Oxidosqualene cyclase is purified from rat liver microsomes by the sequential methods of: 1) solubilization with the detergent lauryl maltoside and 2) FPLC anion-exchange chromatography. Compounds are tested to determine their ability to inhibit the conversion of squalene monoepoxide to lanosterol catalyzed by the purified oxidosqualene cyclase. The reaction mixture (final volume, 200 μl) contains potassium phosphate buffer (50 mM, pH 7.4), Na$_2$EDTA (500 μM), Tween 80 (0.1%), [$^3$H]squalene monoepoxide (10 μM of the racemic mixture, 50 μCi/μmol), test compound (10 μM) and purified oxidosqualene cyclase (50 μg). The reagents, prior to mixing are equilibrated at 37° C. for 10 minutes. The reaction is initiated by adding enzyme. The mixture is incubated for 40 minutes with shaking in a water bath. The reaction is terminated by the addition of 5 ml of CHCl$_3$/MeOH (2:1, v/v), 0.8 ml of water and 10 μg each of squalene monoepoxide, squalene diepoxide, lanosterol and cholesterol. The organic layer is isolated and evaporated to dryness under nitrogen. The residue is dissolved in 200 μl of hexane/ethanol (99:1) and the sample is subjected to HPLC separation using a C$_{18}$ reverse phase column eluted isocratically with 3.6% water in MeOH. Radioactivity is quantitated using an in-line scintillation counter. Oxidosqualene cyclase activity is expressed as the percent inhibition of oxidosqualene cyclase activity at 10 μM test compound (I$_{10}$ values).

Table 1 provides a summary of the testing data for the inhibition of oxidosqualene cyclase by compounds of the present invention.

TABLE 1

| Inhibition of Oxidosqualene Cyclase | | |
|---|---|---|
| Test Compound | I$_{10}$ purified enzyme | IC$_{50}$ HepG2 Cell |
| 102417 | 97% | 0.7 μM |

TABLE 1-continued

| | Inhibition of Oxidosqualene Cyclase | |
|---|---|---|
| Test Compound | $I_{10}$ purified enzyme | $IC_{50}$ HepG2 Cell |
| 100905 | 100% | 52 μM |

102417 = N-(1-Oxododecyl)-8-aza-4α, 10-dimethyl-trans-decal-3β-ol.
100905 = N-[1-Oxo-5-(3-methylbutylmercapto)pentyl]-8-aza-4α, 10-dimethyl-trans-decal-3β-ol.

In a further embodiment, the present invention provides a method of inhibiting cholesterol biosynthesis in a patient in need thereof comprising administering to said patient an effective cholesterol biosynthesis inhibitory amount of a compound of formula (I), formula (II), formula (III) or formula (IV). The present invention also provides a method of lowering plasma cholesterol in a patient in need thereof, and a method of treating a patient afflicted with hypercholesterolemia, comprising administering to said patient an effective hypocholesterolemic amount of a compound of formula (I), formula (II), formula (III) or formula (IV).

It is believed that the compounds of the present invention exert their inhibitory effect on cholesterol biosynthesis through inhibition of squalene epoxidase and/or oxidosqualene cyclase. However, the present invention is not intended to be limited to a particular mechanism of action in achieving inhibition of cholesterol biosynthesis in a patient in need thereof.

As used herein, the term "patient" refers to warm-blooded animals or mammals, including humans. A patient is in need of treatment to inhibit cholesterol biosynthesis or to reduce plasma cholesterol when the patient is suffering from hypercholesterolemia, such as, for example, in the case of a patient suffering from familial hyperlipidemia.

Hypercholesterolemia is a disease state characterized by levels of plasma cholesterol or of LDL cholesterol which are elevated by a clinically significant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by the use of clinical tests, physical examination and medical/family history, those patients who are suffering from hypercholesterolemia and those who are at risk of developing hypercholesterolemia and thus readily determine if an individual is a patient in need of treatment for hypercholesterolemia.

An effective hypocholesterolemic amount of a compound of formula (I), formula (II), formula (III) or formula (IV) is an amount which is effective in reducing plasma cholesterol levels or LDL cholesterol levels in a patient in need thereof. As such, successful treatment of a patient for hypercholesterolemia is understood to include reducing a patient's plasma cholesterol or LDL cholesterol levels. Successful treatment for hypercholesterolemia is also understood to include prophylaxis in preventing clinically significant elevations in plasma cholesterol or in LDL cholesterol levels in a patient who is at risk of the development of hypercholesterolemia.

An effective cholesterol biosynthesis inhibitory amount of a compound of formula (I), formula (II), formula (III) or formula (IV) is an amount which is effective in inhibiting cholesterol biosynthesis in a patient in need thereof which results in the lowering of plasma cholesterol levels or LDL cholesterol levels.

An effective hypocholesterolemic dose or an effective cholesterol biosynthesis inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective hypocholesterolemic amount, and an effective cholesterol biosynthesis inhibitory amount, of a compound of formula (I), formula (II), formula (III) or formula (IV) will generally vary from about 0.1 milligram per kilogram of body weight per day (mg/kg/day) to about 500 mg/kg/day. A daily dose of from about 0.3 mg/kg to about 80 mg/kg is preferred.

In addition, the present invention provides a method of treating a patient afflicted with a fungal infection comprising administering to said patient an effective antifungal amount of a compound of formula (I), formula (II), formula (III) or formula (IV). Certain fungi are dependent on the biosynthesis of endogenous ergosterol for their growth and reproduction as described in "Sterol Biosynthesis Inhibitors; Pharmaceutical and Agrochemical Aspects" Edited by D. Berg and M. Plempel (Ellis Horwood, 1988). By inhibiting the biosynthesis of ergosterol, the compounds of formula (I), formula (II), formula (III) or formula (IV) inhibit the growth and reproduction of fungi and thus provide an antifungal effect.

As used herein, the term "fungal infection" refers to an invasion and multiplication of fungi into the tissues of a patient. Fungal infections for which treatment with a compound of formula (I), formula (II), formula (III) or formula (IV) will be particularly useful for include infections of: *Microsporum canis, Ctenomyces mentagrophytes, Trichophyton rubrum, Phialophora verrucosa, Cryptococcus neoformans, Candida tropicalis, Candida albicans,* Mucor species, *Aspergillus fumigatus, Sporotrichum schenckii* and Saprolegnia species.

An effective antifungal amount of a compound of formula (I), formula (II), formula (III) or formula (IV) refers to an amount which is effective, upon single or multiple administration to the patient, in controlling the growth of the fungus. As used herein, "controlling the growth" of the fungus refers to slowing, interrupting, arresting or stopping its growth or its reproduction, and does not necessarily indicate a total elimination of the fungus.

An effective antifungal dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective antifungal amount of a compound of formula (I), formula (II), formula (III) or formula (IV) will generally vary from about 0.1 milligram per kilogram of body weight per day (mg/kg/day) to about 500 mg/kg/day. Where systemic administration is desired, a daily dose of from about 0.3 mg/kg to about 80 mg/kg is preferred. Where topical administration is desired, a daily dose of from about 5 to about 500 mg and more particularly from about 20 to about 80 mg of the active ingredient are preferred.

In effecting treatment of a patient, compounds of formula (I), formula (II), formula (III) or formula (IV) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

Compounds of formula (I), formula (II), formula (III) or formula (IV) can be administered in the form of pharmaceutical compositions or medicaments which are made by combining the compounds of formula (I), formula (II), formula (III) or formula (IV) with pharmaceutically acceptable carriers or excipients, the proportion and nature of which are determined by the chosen route of administration, and standard pharmaceutical practice.

In another embodiment, the present invention provides compositions comprising a compound of formula (I), formula (II), formula (III) or formula (IV) in admixture or otherwise in association with one or more inert carriers. These compositions are useful, for example, as assay standards, as convenient means of making bulk shipments, or as pharmaceutical compositions. An assayable amount of a compound of formula (I), formula (II), formula (III) or formula (IV) is an amount which is readily measurable by standard assay procedures and techniques as are well known and appreciated by those skilled in the art. Assayable amounts of a compound of formula (I), formula (II), formula (III) or formula (IV) will generally vary from about 0.001% to about 75% of the composition by weight. Inert carriers can be any material which does not degrade or otherwise covalently react with a compound formula (I), formula (II), formula (III) or formula (IV). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of formula (I), formula (II), formula (III) or formula (IV) in admixture or otherwise in association with one or more pharmaceutically acceptable carriers or excipients.

The pharmaceutical compositions or medicaments are prepared in a manner well known in the pharmaceutical art. The carrier or excipient may be a solid, semisolid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of formula (I), formula (II), formula (III) or formula (IV) may be incorporated with excipients and used in the form of tablets, troches, capsules, elixirs, suspensions, syrups, wafers, chewing gums and the like. These preparations should contain at least 4% of the compound of formula (I), formula (II), formula (III) or formula (IV), the active ingredient, but may be varied depending upon the particular form and may conveniently be between 4% to about 70% of the weight of the unit. The amount of the active ingredient present in compositions in such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents; such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of formula (I), formula (II), formula (III) or formula (IV) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of formula (I), formula (II), formula (III) or formula (IV) in their end-use application.

Preferred groups for compounds of formula (I) are the following: E is O, A is a $C_5$ alkylene, Y is S, B is a $C_2$ alkylene, D is —$CH(CH_3)_2$. Preferred groups for compounds of formula (II) are the following: E is O, A is a $C_5$ alkylene, Y is S, D is phenyl. Preferred groups for compounds of formula (III) are the following: E is O, A is a $C_8$–$C_{10}$ alkylene, D is methyl or phenyl. Preferred groups for compounds of formula (IV) are the following: E is O, $D_1$ is methyl.

The following specific compounds of formula (I), formula (II), formula (III) or formula (IV) are particularly preferred in the end-use application of the compounds of the present invention:

N-[1-Oxo-5-(3-methylbutylmercapto)pentyl]-8-aza-4α,10-dimethyl-trans-decal-3β-ol;

N-[1-Oxo-5-(phenylmethylmercapto)pentyl]-8-aza-4α,10-dimethyl-trans-decal-3β-ol;

N-[1-Oxo-5-(phenylmercapto)pentyl]-8-aza-4α,10-dimethyl-trans-decal-3β-ol;

N-(1-Oxododecyl)-8-aza-4α,10-dimethyl-trans-decal-3β-ol;

N-(1-Thioxododecyl)-8-aza-4α,10-dimethyl-trans-decal-3β-ol.

What is claimed is:

1. A compound of the formula

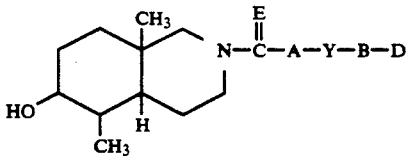

wherein
E is O or S
A is a saturated $C_1$–$C_{14}$ alkylene of straight or branched chain configuration;
Y is oxygen, sulfur, sulfinyl or sulfonyl;
B is a saturated $C_1$–$C_{14}$ alkylene of straight or branched chain configuration; and
D is a $C_1$–$C_4$ saturated or unsaturated alkyl of straight or branched chain configuration, —$CF_3$, —$CHF_2$, —$CH_2F$, or phenyl.

2. A method of inhibiting the biosynthesis of cholesterol in a patient in need thereof comprising administering to said patient an effective cholesterol biosynthesis inhibiting amount of a compound of claim 1.

3. A method of lowering plasma cholesterol in a patient in need thereof comprising administering to said patient an effective hypocholesterolemic amount of a compound of claim 1.

4. A method of treating a patient afflicted with hypercholesterolemia comprising administering to said patient an effective hypocholesterolemic amount of a compound of claim 1.

5. A composition comprising an assayable amount of a compound of claim 1 in admixture or otherwise in association with an inert carrier.

6. A pharmaceutical composition comprising an effective hypocholesterolemic amount of a compound of claim 1 in admixture or otherwise in association with one or more pharmaceutically acceptable carriers or excipients.

7. A compound of claim 1 wherein E is O.

8. A compound of claim 7 wherein Y is S.

9. A compound of claim 1 wherein the compound is N-[1-Oxo-5-(3-methylbutylmercapto)pentyl]-8-aza-4α,10-dimethyl-trans-decal-3β-ol.

* * * * *

UNITED STATES PATENT AND TRADEMARK OFFICE
CERTIFICATE OF CORRECTION

PATENT NO. : 5,084,461                  Page 1 of 3

DATED : January 28, 1992

INVENTOR(S) : Marion W. Wannamaker, et al.

It is certified that error appears in the above-identified patent and that said Letters Patent is hereby corrected as shown below:

```
Column 3, Line 31 the patent reads: "CH2F," and should
read -- -CH2F,--

Column 4, line 6 the patent reads: "-CH2(CH2)3CH2-, and
should read -- -CH2(CH2)3CH2- --.

Colum 9, line 21 the patent reads: "in vacuo to to" and
should read --in vacuo to--.

Column 10, line 1 the patent reads: "Heat at 0° C." and
should read --Heat at 40°C--.

Column 10, line 33 the patent reads: "N-[1-Thioxo5" and
should read --N-[1-Thioxo-5--.

Column 11, line 49 the patent reads: "funtionality" and
should read --functionality--.

Column 13, line 17 the patent reads: "and with water" and
should read --and wash with water--.

Column 14, line 35 the patent reads: "(2.83 g, mmol) and
should read --(2.83g, 7mmol)--.
```

UNITED STATES PATENT AND TRADEMARK OFFICE
CERTIFICATE OF CORRECTION

PATENT NO. : 5,084,461

DATED : January 28, 1992

INVENTOR(S) : Marion W. Wannamaker, et al.

It is certified that error appears in the above-identified patent and that said Letters Patent is hereby corrected as shown below:

```
Column 22, lines 49-53 the patent reads: "dimethyl-decal-
dimethyl-decal-3-acetate of structure (23) or N-
thioformate-8-aza-4, 10-dimethyl-decal-3-ol of structure
(24) or N-thioformate-8-aza-4, 10-dimethyl-decal-3-1 of
structure (24) as described previously in Scheme A,
optional step e2." and should read
--dimethyl-decal-3-acetate of structure (23) or N-
thioformate-8-aza-4, 10-dimethyl-decal-3-acetate of
structure (23) as described previously in Scheme A,
optional step e2.--.

Column 23, lines 34 and 35 the patent reads:
                         "EXAMPLE 17
                              "
and should read
                         --EXAMPLE 17
N-Formyl-8-aza-4α,10-dimethyl-trans-decal-3β-ol--
```

UNITED STATES PATENT AND TRADEMARK OFFICE
CERTIFICATE OF CORRECTION

PATENT NO. : 5,084,461
DATED : January 28, 1992
INVENTOR(S) : Marion W. Wannamaker, et al It is certified that error appears in the above-indentified patent and that said Letters Patent is hereby corrected as shown below:

Column 23, line 63, "to described" should read --to those described--

Signed and Sealed this

Fourteenth Day of June, 1994

Attest:

BRUCE LEHMAN

*Attesting Officer*   *Commissioner of Patents and Trademarks*